United States Patent [19]

Stroman et al.

[11] Patent Number: 4,879,231
[45] Date of Patent: * Nov. 7, 1989

[54] TRANSFORMATION OF YEASTS OF THE GENUS PICHIA

[75] Inventors: David W. Stroman, Bartlesville, Okla.; James M. Cregg; Michael M. Harpold, both of San Diego, Calif.; George T. Sperl, Gurnee, Ill.

[73] Assignee: Phillips Petroleum Company, Bartlesville, Okla.

[ * ] Notice: The portion of the term of this patent subsequent to Jun. 6, 2006 has been disclaimed.

[21] Appl. No.: 666,579

[22] Filed: Oct. 30, 1984

[51] Int. Cl.$^4$ .................. C12N 15/00; C12N 5/00; C12N 7/00

[52] U.S. Cl. ................... 435/172.3; 435/255; 435/256; 435/172.1; 435/320; 935/28; 935/56; 935/69

[58] Field of Search .............. 435/68, 172.3, 255, 435/317, 320, 256, 107, 172.1; 536/27; 935/6, 14, 28, 37, 56, 69

[56] References Cited

U.S. PATENT DOCUMENTS 4,617,274 10/1986 Wegner .......................... 435/255

OTHER PUBLICATIONS

Hinnen et al., 1978, *Pnc Natl Acad. Sci.*, vol. 75, pp. 1929–1933, "Transformation of Yeast".
Sherman et al., 1982, *Methods in Yeast Genetics*, Cold Spring Harbor, NY, pp. 114–115.
Russell et al., *J. Biol Chem*, Jan. 1983, vol. 258, pp. 143–149, "The Primary Structure of the Alcohol Dehydrogenase Gene from the Fission Yeast Schizosaccharomyces Pombe".
Donohue et al., Gene, vol. 18, pp. 47–59, "The Nucleotide Sequence of the HISY Region of Yeast".
Stinchomb et al., *Proc. Natl Acad Sci*, 1980, vol. 77, pp. 4559–4563, "Eukaryotic DNA Segments Capable of Autumous Replication in Yeast".

*Primary Examiner*—Robin Teskin
*Attorney, Agent, or Firm*—J. E. Phillips

[57] ABSTRACT

Process for transforming yeast strains of the genus *Pichia* is disclosed. Novel yeast strains of the genus *Pichia* which can be transformed with recombinant DNA material are also disclosed. In addition, a method for isolating functional genes and other functional DNA sequences from yeast strains of the genus *Pichia* is described.

18 Claims, 6 Drawing Sheets

TRANSFORMATION OF YEASTS OF THE GENUS PICHIA

BACKGROUND

This invention relates to the field of recombinant DNA technology. In one of its aspects, the invention relates to novel yeast strains. In another aspect, the invention relates to processes for transforming yeast strains with recombinant DNA material.

Up to now, commercial efforts employing recombinant DNA technology for producing various polypeptides have centered on *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the proteolytic activities of *E. coli* can seriously limit yields of some useful products. These and other considerations have led to increased interest in alternative hosts, in particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale fermentations for centuries, as compared to the relatively recent advent of large scale *E. coli* fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. Pat. No. 4,414,329 (assigned to Phillips Petroleum Co.). Additional advantages of yeast hosts include the fact that many critical functions of the organism, e.g., oxidative phosphorylation, are located within organelles, and hence not exposed to the possible deleterious effects of the organism's production of polypeptides foreign to the wild-type host cells. As a eukaryotic organism, yeast may prove capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host/vector systems is severely hampered by the lack of knowledge about transformation conditions and suitable vectors. In addition, auxotrophic mutations are often not available, precluding a direct selection for transformants by auxotrophic complementation. If recombinant DNA technology is to fully sustain its promise, new host/vector systems must be devised which facilitate the manipulation of DNA as well as optimize expression of inserted DNA sequences so that the desired polypeptide products can be prepared under controlled conditions and in high yield.

OBJECTS OF THE INVENTION

An object of our invention, therefore, is the transformation of yeast of the genus Pichia.

Another object of our invention is a host of the genus Pichia suitable for transformation with recombinant DNA material.

These and other objects of the invention will become apparent from the disclosure and claims herein provided.

STATEMENT OF THE INVENTION

In accordance with the present invention, we have developed a process for the transformation of yeast cells of the genus Pichia. By the practice of the transformation process of the present invention, DNA sequences can be introduced into host cells of the genus allowing Pichia to be employed as a host system for the production of polypeptide product in yeast. Further, in accordance with the present invention, novel strains of microorganisms of the genus Pichia are provided. These novel strains are useful as hosts for the introduction of recombinant DNA material into yeast.

In accordance with another embodiment of the invention, the novel strains of microorganisms of the genus Pichia are employed in a process for the isolation of functional genes and other functional DNA sequences from yeast strains of the genus Pichia. BRIEF DESCRIPTION OF THE DRAWINGS FIG. 1 is a restriction map of plasmid pYA2.
FIG. 2 is a restriction map of plasmid YEp13.
FIG. 3 is a restriction map of plasmid pYA4.
FIG. 4 is a restriction map of plasmid pYJ30.
FIG. 5 is a restriction map of plasmid pYJ32.
FIG. 6 is a restriction map of plasmid pSAOH5.

The following abbreviations are used throughout this application to represent the restriction enzymes employed:

| Abbreviation | Restriction Enzyme |
| --- | --- |
| B | BamHI |
| B$_2$ | BglII |
| H$_3$ | HindIII |
| Nr | NruI |
| Ps | PstI |
| R$_1$ | EcoRI |
| R$_5$ | EcoRV |
| S | SalI |
| Sm | SmaI |
| Sp | SphI |
| S$_3$ | Sau3AI |
| Xh | XhoI |

The convention employed in the Figures is to show in parentheses a restriction enzyme site which was used for construction of the DNA sequence but was destroyed upon ligation of the construct.

DETAILED DESCRIPTION OF THE INVENTION

Figure 1:
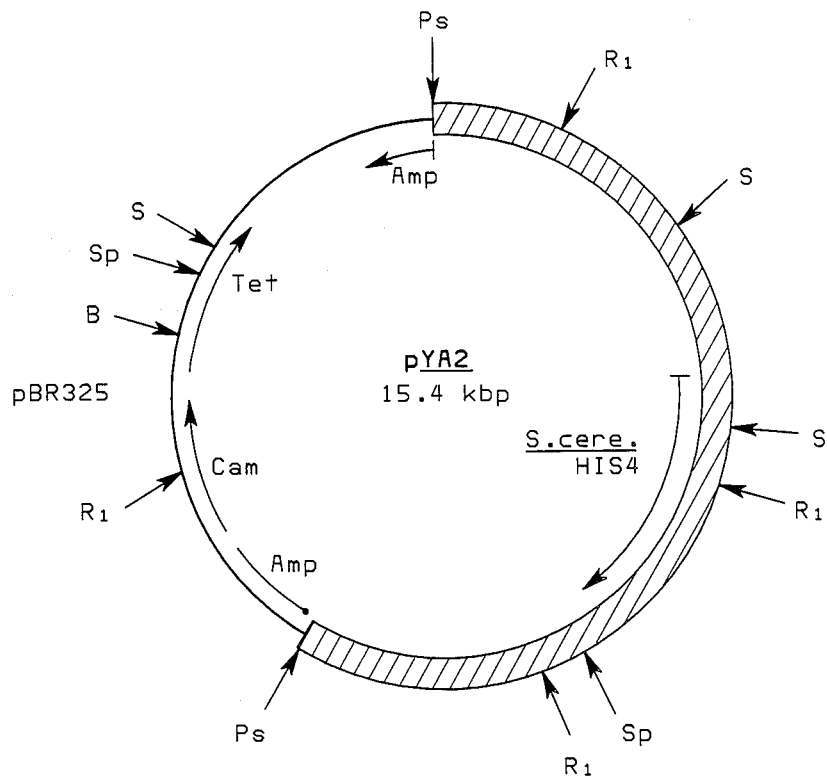

In accordance with the present invention, a transformation procedure for the introduction of recombinant DNA material into host cells of the genus Pichia is provided.

Further in accordance with the present invention, novel yeast strains of the genus Pichia are provided which are useful as hosts for the introduction of recombinant DNA In accordance with another embodiment of the invention, a method is provided for the isolation of functional genes and other functional DNA sequences from the genome of yeasts of the genus Pichia.

Development of *Pichia pastoris* Transformation System

The transformation of *Pichia pastoris* has not been previously described. The experimental procedures for transformation of *Pichia pastoris* are presented in greater detail below (Example III). In order to develop a transformation system for *P. pastoris*, the auxotrophic mutant GS115 (NRRL Y-15851) was isolated and determined to be defective in the histidine pathway in that the strain has no detectable histidinol dehydrogenase activity. (See assay procedure in Example II).

Those of skill in the art recognize that mutation frequencies can be increased in a variety of ways, such as, for example, by subjecting exponentially growing cells to the action of a variety of mutagenic agents, such as, for example, N-methyl-N'-nitro-N-nitrosoguanidine, ethyl methanesulfonate, ultraviolet irradiation and the like. Isolation and identification of mutant strains defective in a specific metabolic pathway can be accomplished by determining the nutrient or nutrients required by the strain for growth as detailed, for example, in Example I. The specific gene and gene product in which a mutant strain is defective can then be determined by identifying the enzymatic activity which is absent, as detailed, for example, in Example II.

Yeast strains of the genus Pichia, and especially mutant Pichia strains of the invention can be transformed by enzymatic digestion of the cell walls to give spheroplasts; the spheroplasts are then mixed with the transforming DNA and incubated in the presence of calcium ions and polyethylene glycol, then regenerated in selective growth medium. The transforming DNA includes the functional gene in which the host strain is defective, thus only transformed cells survive on the selective growth medium employed.

To prepare Pichia spheroplasts, the cells are first contacted with a sulfhydryl group reducing agent, such as, for example, dithiothreitol or β-mercaptoethanol. An example of a specific solution containing a sulfhydryl group reducing agent is the dithiothreitol in SED buffer described in the Examples. Enzymatic digestion of the cell walls can then be accomplished by contacting the strain to be transformed with any of the many cell wall degrading reagents known to those of skill in the art, such as for example Zymolyase (Miles Laboratories), Glusulase (Endo Laboratories), and the like. Although a wide variety of temperatures, contact times and dosage levels are operable, generally, when using, for example, Zymolyase 60,000 (60,000 units/g) about 10 up to about 100 μg of cell wall degrading reagent per 10 mL of cell suspension are employed for spheroplast formation. Preferably about 40–50 μg of Zymolyase 60,000 per 10 mL of cell suspension is employed. Temperature is generally maintained at about 25° C. or above, but less than about 35° C. Preferably, temperature is maintained at about 30° C. Contact time is generally at least about 15 minutes and usually no greater than about 60 minutes. While many buffered media are suitable, it is essential that cells to be converted to spheroplasts be suspended in a buffer which is iso-osmotic with the cells, such as, for example, SCE buffer (sorbitol/citrate/EDTA; see Examples for recipe).

The spheroplasts can be transformed by contact with virtually any amount of recombinant DNA material. Generally, at least about 0.01 μg of transforming DNA per 100 μL of spheroplast containing solution (containing between about $1–3 \times 10^7$ spheroplasts per 100 μL) are employed. Where only small amounts of recombinant DNA material are available, sonicated *E. coli* DNA can be used to supplement the amount of available DNA, thereby improving transformation frequencies by minimizing the handling losses of recombinant DNA material during experimental manipulation.

Transformed spheroplasts are then treated under cell wall regenerating conditions. Cell wall regenerating conditions comprise adding a sample containing transformed spheroplasts to melted regeneration agar maintained at about 40–60° C. A typical regeneration agar provides a balanced osmotic media and comprises:

| | |
|---|---|
| sorbitol | about 1 M |
| dextrose | about 0.1 M |
| yeast nitrogen base | about 7 g/L |
| Bacto-agar | about 3% |

The transformed spheroplasts in melted regeneration agar are poured over a bottom layer of regeneration agar and then incubated at about 25–35° C. for about 3–10 days.

*Pichia pastoris* NRRL Y-15851 (GS115) has been transformed with a number of plasmids. Several of these plasmids are novel and have therefore been made available to the public by deposition with the Northern Regional Research Center in Peoria, Ill. Plasmids and their accession numbers are tabulated below (all plasmids have been deposited in an *E. coli* host).

| Plasmid | Inventor strain designation | NRRL accession number |
|---|---|---|
| pYA2 | LE392-pYA2 | B-15874 |
| pYJ30 | LE392-pYJ30 | B-15890 |
| pYJ32 | LE392-pYJ32 | B-15891 |
| pSAOH5 | MC1061-pSAOH5 | B-15862 |

Figure 2:
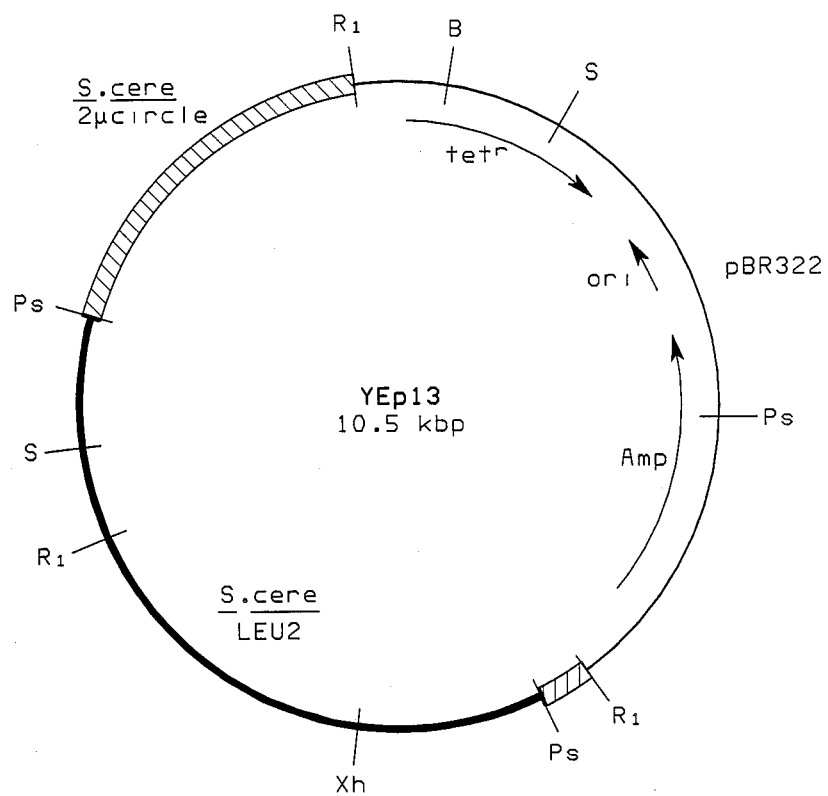
Figure 3:
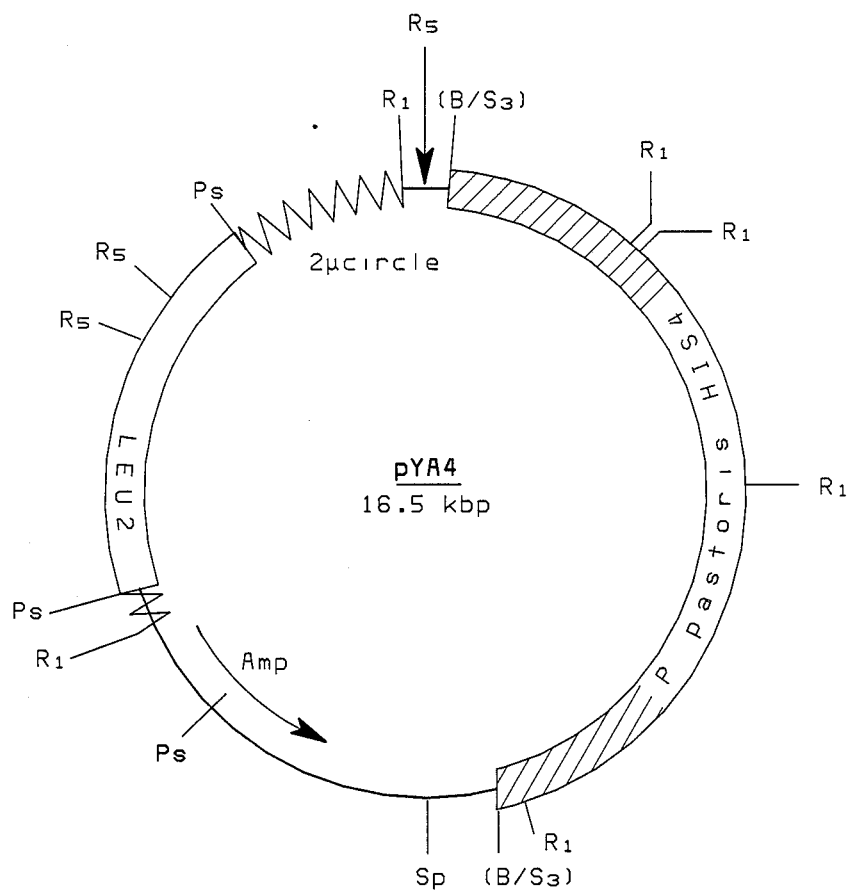

Also used to transform GS115 was plasmid pYA4, which is derived from the *S. cerevisiae* - *E. coli* shuttle vector YEp13 (available from ATCC #37115; see FIG. 2). Thus, plasmid pYA4 is YEp13 plus a 6.0 kbp Sau3A partial digestion fragment of *Pichia pastoris* chromosomal DNA which includes the HIS4 gene (see FIG. 3) ligated into the unique BamHI site of YEp13.

Plasmid pYA2 (see FIG. 1) contains pBR325 DNA sequences and a 9.3 kbp *S. cerevisiae* PstI fragment which includes the *S. cerevisiae* HIS4 gene. It was surprisingly found that the *S. cerevisiae* HIS4 gene in plasmid pYA2 functioned in Pichia. An additional surprising observation was the fact that pYA2, which transforms *S. cerevisiae* at low frequency by integrative recombination, transformed Pichia at high frequency and was maintained as an extrachromosomal element in NRRL Y-15851 over a number of generations of growth.

Figure 4:
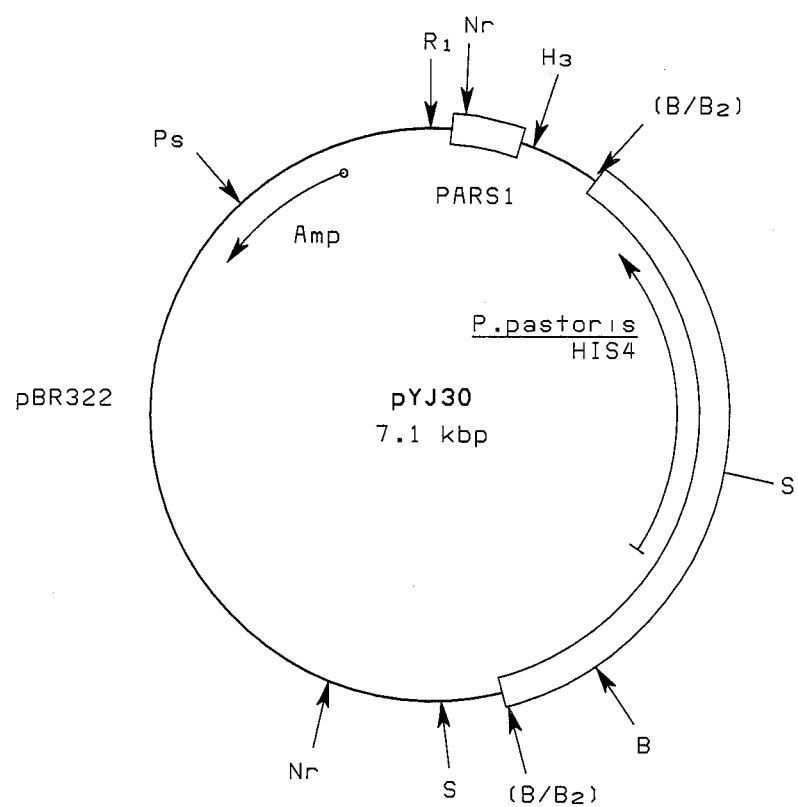
Figure 6:
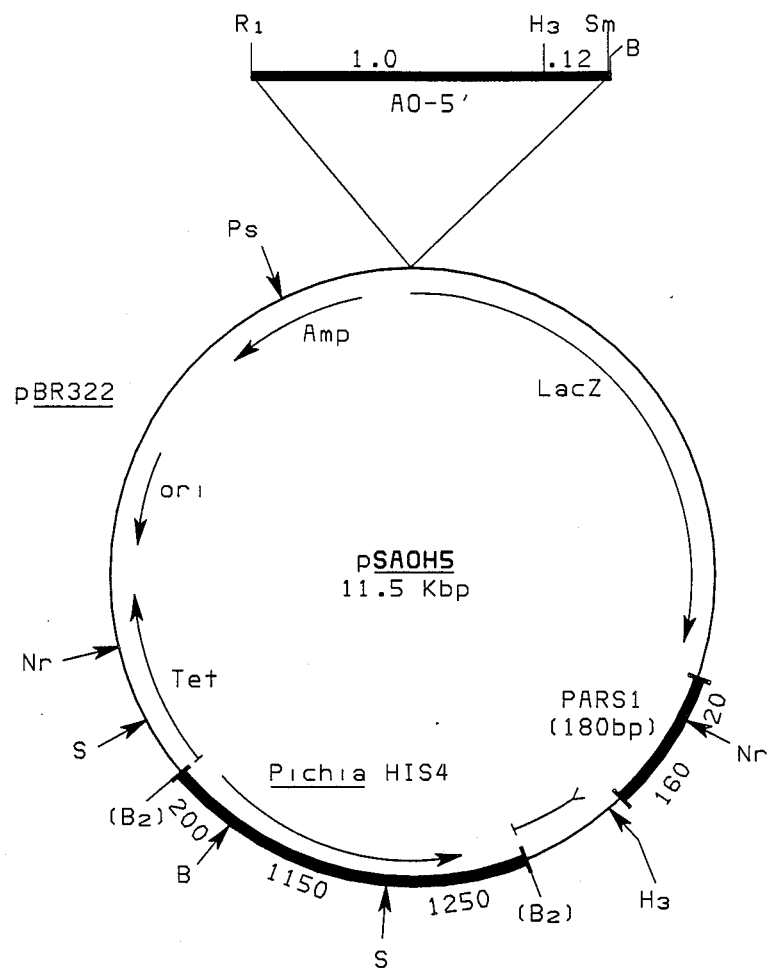

Plasmid pYJ30, shown in FIG. 4, has pBR322 DNA sequences, a 2.7 kbp BglII fragment of Pichia chromosomal DNA which has the Pichia HIS4 gene and a 164 bp TaqI fragment of Pichia chromosomal DNA which has autonomous replication sequence activity (PARS1). This plasmid has also been used to transform NRRL Y-15851 (GS115), and transformation occurs at high frequency. This plasmid is useful for introducing recombinant DNA material into a Pichia host. For example, plasmid pSAOH5 (see FIG. 6) is derived from this plasmid by insertion of the E. coli LacZ gene and the alcohol oxidase regulatory region at the unique $R_1$ site of pYJ30. Plasmid pSAOH5 is shown in Example IV below to be capable of producing a polypeptide product not native to the host cell in Pichia pastoris.

Figure 5:
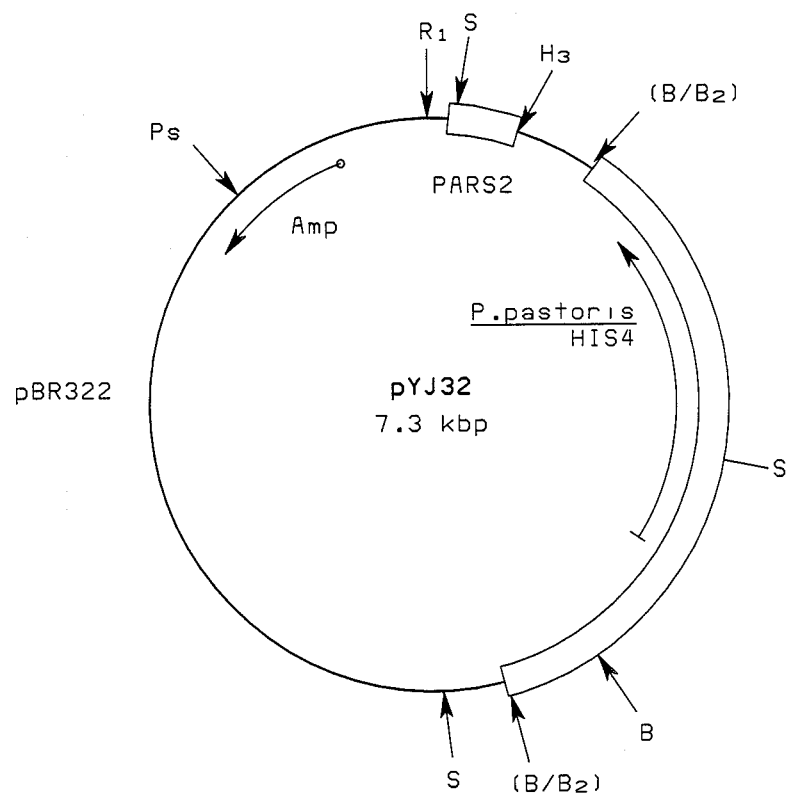

Plasmid pYJ32, shown in FIG. 5, is similar to pYJ30, except the autonomous replication activity is provided by PARS2, a 385 bp TaqI fragment of Pichia chromosomal DNA. This plasmid is also capable of transforming Pichia pastoris NRRL Y-15851 at high frequencies.

The transformation of yeast strains of the genus Pichia, as demonstrated herein, makes possible the introduction of recombinant DNA material into yeast hosts. As further detailed in the examples which follow, transformed yeast strains of the genus Pichia are useful, for example, for the production of polypeptide products by a yeast host.

In accordance with another embodiment of the present invention, there is provided a method for isolation of functional genes and other functional DNA sequences from yeast strains of the genus Pichia. For the isolation of functional genes, the method comprises complementation of a defective Pichia pastoris strain with cloned fragments of Pichia chromosomal DNA, selection of transformed strains which survive selective growth conditions, wherein the selective growth conditions comprise minimal media absent the gene product required by the defective host strain for growth, isolation and recovery of Pichia DNA inserts from the plasmids contained in the selected transformed strains. For example, one could isolate the Pichia LEU2 gene by transforming a leu2 P. pastoris mutant with a library of Pichia chromosomal DNA and selecting for transformed strains which survive in the absence of leucine supplementation of the media. Similarly, one could isolate the Pichia ARG4 gene by transforming an appropriate P. pastoris mutant with a library of Pichia chromosomal DNA and proceeding as above, except the selection media would be absent histidine or arginine supplementation, respectively.

Those of skill in the art recognize that other functional DNA sequences can be isolated using the transformation system of the present invention. Such sequences include:
autonomous replication sequences (ARSs),
centromeric sequences (CENs)
chromosomal terminii (telomeres),
promoters and regulatory sequences,
transcription and translation terminators, and the like.

EXAMPLES

The buffers and solutions employed in the following examples have the compositions given below:

| | |
|---|---|
| 1 M Tris buffer | 121.1 g Tris base in 800 mL of $H_2O$; adjust pH to the desired value by adding concentrated (35%) aqueous HCl; allow solution to cool to room temperature before final pH adjustment; dilute to a final volume of 1 L. |
| TE buffer | 1.0 mM EDTA in 0.01 M (pH 7.4) Tris buffer |
| YPD Medium | 1% Bacto-yeast extract<br>2% Bacto-peptone<br>2% Dextrose |
| SD Medium | 6.75 g yeast nitrogen base without amino acids (DIFCO)<br>2% Dextrose<br>in 1 L of water |
| SED | 1 M Sorbitol<br>25 mM EDTA<br>50 mM DTT |
| SCE Buffer | 9.1 g Sorbitol<br>1.47 g Sodium citrate<br>0.168 g EDTA<br>50 mL $H_2O$<br>-pH to 5.8 with HCl |
| CaS | 1 M Sorbitol<br>10 mM $CaCl_2$<br>-filter sterilize |
| PEG Solution | 20% polyethylene glycol-3350<br>10 mM $CaCl_2$<br>10 mM Tris-HCl (pH 7.4)<br>-filter sterilize |
| SOS | 1 M Sorbitol<br>0.3x YPD medium<br>10 mM $CaCl_2$ |
| MM (minimal medium) | 0.875 g $KH_2PO_4$<br>0.125 g $K_2HPO_4$<br>1.0 g $(NH_4)_2SO_4$<br>0.5 g $MgSO_4.7H_2O$<br>0.1 g NaCl<br>0.05 mg $FeCl_3.6H_2O$<br>0.07 mg $ZnSO_4.7H_2O$<br>0.01 mg $H_3BO_3$<br>0.01 mg $CuSO_4.5H_2O$<br>0.01 mg KI<br>0.1 g $CaCl_2.2H_2O$<br>-per liter of sterile $H_2O$ |
| MM "minus" | MM formulation without $(NH_4)_2SO_4$ |
| Citrate buffer | 9.79 g sodium citrate<br>3.2 g citric acid<br>-dilute to 500 mL with $H_2O$<br>-adjust to pH 5.5 with 1 N NaOH |
| Nystatin solution | 4.4 mg nystatin (5680 Units/mg)<br>1 mL dimethyl formamide<br>-dilute to 10 mL with water |
| E Buffer | 50 mM Tris-HCl(pH 7.4)<br>0.01 mM histidinol<br>50 mM $MgSO_4$<br>1 mM DTT |
| Vitamin Mix | p-aminobenzoic acid 50 mg/100 mL<br>p-hydroxybenzoic acid 50<br>riboflavin 25<br>pantothenate 50<br>$B_{12}$ 1<br>folic acid 50<br>pyridoxine 50<br>biotin 5<br>thiamine 10<br>nicotinic acid 50<br>inositol 2000 |

The following abbreviations are used throughout the example, with the following meaning:

| | |
|---|---|
| NTG | N—methyl-N'—nitro-N—nitrosoguanidine |
| DTT | dithiothreitol |
| NAD | nicotinamide adenine dinucleotide |
| SDS | sodium dodecyl sulfate |
| ala | alanine |
| arg | arginine |
| asn | asparagine |
| asp | aspartic acid |
| cys | cysteine |
| glu | glutamic acid |
| gln | glutamine |
| gly | glycine |
| his | histidine |
| ile | isoleucine |
| leu | leucine |
| lys | lysine |
| met | methionine |
| phe | phenylalanine |
| pro | proline |
| ser | serine |
| thr | threonine |
| trp | tryptophan |

| | | |
|---|---|---|
| tyr | tyrosine | |
| val | valine | |

EXAMPLE I

Isolation of Auxotrophic Mutants

A. Pichia Mutagenesis

Culture of a selected yeast strain, such as for example, *Pichia pastoris* NRRL Y-11430, was inoculated into 100 mL of YPD broth and incubated at 30° C. on a shaker for about 12-20 hrs. About 40 mL of the resulting culture were spun down at about 2,000 g for 5 minutes. The cells were then washed twice with 40 mL aliquots of sterile 0.1 M citrate buffer (pH 5.5). Washed cells were resuspended in 36 mL of sterile citrate buffer, then treated with 4 mL of NTG solution containing 5 mg of NTG per mL—thus giving a final NTG concentration of 500 μg/mL. Cells in the presence of NTG were allowed to stand for about 30 minutes at room temperature without agitation.

NTG was then removed by washing the cells twice with 40 mL aliquots of sterile deionized water. Sufficient YPD medium was used to resuspend washed cells, which were then transferred to a flask and total volume brought up to 100 mL with additional YPD. These mutagenized cells were then incubated at 30° C. on a shaker for about 48 hours.

After incubation, about 40 mL of the yeast containing solution were spun down at 2,000 g for 5 minutes. The cell pellet was washed twice with 40 mL aliquots of sterile, deionized water, then suspended in 40 mL of MM "minus" media plus 1% glucose carbon source and 5 μg biotin and incubated at 30° C. on a shaker for 12-20 hours. B. Nystatin enrichment Five mL of the above culture grown on glucose was used to inoculate 100 mL of "restricted media". Restricted media comprises the MM formulation plus carbon source (typically 1% glucose), vitamin/amino acid supplementation as appropriate (such as the "vitamin mix" referred to above), except no supplementation is provided for the metabolite produced by the biosynthetic pathway in which a defect is sought. For example, where a leucine auxotroph is desired, no leucine supplementation will be provided. The inoculum in restricted media was incubated at 30° C. in a shake flask and monitored periodically on a Klett-Summerson photoelectric colorimeter equipped with a 500-570 millimicron green filter. Incubation was continued until the scale reading (which is proportional to optical density) has increased 20-30% with respect to the original scale reading.

When the scale reading had increased as desired, the solution was treated with 1 mL of Nystatin solution, giving a Nystatin content of about 25 units/mL in the solution. The Nystatin-treated solution was incubated at 30° for 90 minutes without agitation, at which time 40 mL of the solution was spun down and the cells washed twice with 40 mL aliquots of deionized water. Washed cells were then diluted as appropriate in order to obtain about 100-150 colonies per plate. Colonies were plated on mutant growth media which consisted of MM media, carbon source (typically 1% glucose), 5 μg biotin and supplementation for any metabolite produced by the biosynthetic pathway in which the mutational defect is sought.

The colonies plated on mutant growth media were replica plated onto media formulation absent the metabolite supplementation. The original and replica plates were incubated at 30° for at least 48 hours. Those colonies that grew on the original plate (on mutant growth media) but not on the replica plates were selected for further characterization.

The auxotrophic mutants selected were transferred to metabolic pool plates and incubated at 30° C. for at least 48 hours in order to determine in which pathway(s) mutational defects existed.

Pool plates were prepared by dissolving 10 mg/mL of the L-isomer of each of 5 different amino acids, as follows:

| | 1 | 2 | 3 | 4 | 5 |
|---|---|---|---|---|---|
| 6 | gly | asn | cys | met | gln |
| 7 | his | leu | ile | val | lys |
| 8 | phe | tyr | trp | thr | pro |
| 9 | glu | ser | ala | asp | arg |

Thus, plate 1 contains 10 mg/mL each of glycine, histidine, phenylalanine and glutamic acid; plate 2 contains 10 mg/mL each of asparagine, leucine, tyrosine and serine, and so on. A tenth plate was prepared by dissolving 1 g of Casamino acids in 1 L of sterile water.

An aliquot of 250 μL of each of amino acid pools 1-10 was applied to plates containing minimal media plus 1% glucose, and the plates allowed to dry overnight.

The mutational defect of a given mutant can be determined by inspection of the growth pattern on the various pool plates. Thus GS115, a mutant defective in the histidine pathway, grew only on plates 1, 7 and 10, but not on the other pool plates which do not provide histidine supplementations. Similarly, GS190, a mutant defective in the arginine pathway, grew only on pool plates 5, 9 and 10, but did not grow on the other pool plates which did not have arginine supplementation.

EXAMPLE II

Identification of *Pichia pastoris* Mutants Defective in Histidinol Dehydrogenase Activity A. Plate Test Initial screening of histidine requiring mutants prepared as described in Example I was carried out to identify mutants defective at the his4C locus (i.e., lacking histidinol dehydrogenase activity). A master plate of histidine auxotrophic mutants was prepared with MM media, 1% glucose, vitamin mix (1 mL per L of media) and 0.2% Casamino acids. The master plate was incubated at 30° C. for at least 48 hours, then four replica plates were prepared from the master plate:

(1) MM "minus" +5 μg biotin +1% glucose +0.2% histidinol (2) MM media +5 μg biotin +1% glucose +0.0002% histidinol (3) MM "minus" +5 μg biotin +1% glucose +0.2% histidine (4) MM media +5 μg biotin +1% glucose +0.002% histidine These 4 plates were incubated at 30° C. for at least 48 hours. Those colonies which grew on plates (3) and (4), but did not grow on plates (1) or (2) were selected for further analysis. B. Enzymatic Analysis The first step in the histidinol dehydrogenase assay procedure was to grow a 200 mL culture of a strain in YPD medium with shaking at 30° C. to an $OD_{600}$ of 1.0. The culture was then centrifuged at 2000 g for 5 minutes and the cells were resuspended in 200 mL of SD medium and incubated with shaking at 30° C. After 6–12 hours the culture was harvested by centrifugation and the cell pellet stored at −20° C.

The next step was to prepare a cell extract from the culture. Approximately 1 gram (wet weight) of cells was washed 2 times in 10 mL of cold $H_2O$ (4° C.) and resuspended in 0.83 mL of cold E buffer. To rupture the cells, the sample was passed through an Aminco French pressure cell which had a 0.374 inch diameter piston using an Aminco French press at 20,000 PSI. The pressure cell was held on ice until use and the procedure was performed in a cold room (4° C.). To monitor cell breakage, a 10 μL sample was added to 10 mL of $H_2O$ and its $OD_{600}$ determined and compared to an identically prepared control sample which had not been passed through the pressure cell. If the optical density of the treated sample was greater than 50% of the control, the sample was subjected to the disruption procedure a second time. The extract was then centrifuged in a Beckman SW50.1 rotor at 35,000 rpm and 4° C. for 30 minutes to remove cell debris. The supernatant was removed, mixed with an equal volume of 4° C. glycerol and stored at −20° C.

The concentration of total protein in an extract was estimated using the Bio-Rad Laboratories protein assay method. For this the Bio-Rad Dye Reagent Concentrate was diluted with four volumes of deionized $H_2O$ and filtered through Whatman 3MM paper. A standard concentration curve was then prepared by adding 3, 10, 30, and 100 μg of bovine serum albumin (BSA) in 100 μL E buffer with 50% glycerol to a set of 13×100 mm glass tubes, each of which contained 2.5 mL of the dye reagent. The samples were mixed and held at room temperature for 5 minutes and their optical densities at 595 nm determined. For analyses of the extract, 3, 10, and 30 μL samples were brought to 100 μL with a solution containing E buffer and 50% glycerol and assayed for protein content as described above. A protein concentration value for each extract was then interpolated using the BSA concentration curve.

The final step in the histidinol dehydrogenase activity assay was to measure histidinol dehydrogenase activity in an extract by measuring spectrophotometerically the reduction of AND which occurs in the presence of histidinol. For each extract to be assayed, a reaction mixture which contained 3 mL of $H_2O$, 0.5 mL of 0.5 M glycine (pH 9.4), 0.5 mL of 5 mM $MnCl_2$ and 0.5 mL of 0.1 M AND was prepared on ice. A 2.25 mL aliquot of this mix was added to 2 13×100 mm glass tubes which were on ice. A sample which contained between 50 to 500 μg of protein was added to each of the tubes and the tubes were incubated at 25° C. After 5 minutes the reaction was started by the addition of 0.25 mL of 0.15 M histidinol to one tube and 0.25 mL of $H_2O$ to the other. The optical density of each reaction tube at 340 nm was determined at times of 0.0, 0.5, 1.0 and 2.0 hours. As controls, extracts prepared from *Pichia pastoris* NRRL Y-11430 and *Saccharomyces cerevisiae* 5799-4D (NRRL Y-15859) were assayed in parallel. The net $OD_{340}$ value for each time point was determined by subtracting the value obtained from the sample incubated without histidinol from the value obtained from the sample incubated with histidinol.

While *Pichia pastoris* NRRL Y-11430, a wild type strain requiring no amino acid supplementation, gave an $OD_{340}$ of about 0.25, 0.38 and 0.75 at 0.5, 1.0 and 2.0 hours, respectively, the control his4C mutant (*S. cerevisiae* NRRL Y-15859) gave an $OD_{340}$ of essentially zero at all time points. One such *Pichia pastoris* mutant, designated GS115 and deposited with the Northern Regional Research Center having the accession number NRRL Y-15851, similarly gave an $OD_{340}$ of essentially zero at all time points. Consistent with the mutant genotype nomenclature employed for *S. cerevisiae*, GS115 has been designated as a his4C mutant strain.

EXAMPLE III

*Pichia pastoris* Transformation Procedure

A. Cell Growth

1. Inoculate a colony of *Pichia pastoris* GS115 (NRRL Y-15851) into about 10 mL of YPD medium and shake culture at 30° C. for 12–20 hrs.

2. After about 12–20 hrs., dilute cells to an $OD_{600}$ of about 0.01–0.1 and maintain cells in log growth phase in YPD medium at 30° C. for about 6–8 hrs.

3. After about 6–8 hrs, inoculate 100 mL of YPD medium with 0.5 mL of the seed culture at an $OD_{600}$ of about 0.1 (or equivalent amount). Shake at 30° C. for about 12–20 hrs.

4. Harvest culture when $OD_{600}$ is about 0.2–0.3 (after approximately 16–20 hrs) by centrifugation at 1500 g for 5 minutes. B. Preparation of Spheroplasts 1. Wash cells once in 10 mL of sterile water. (All centrifugations for steps 1–5 are at 1500 g for 5 minutes.)

2. Wash cells once in 10 mL of freshly prepared SED.

3. Wash cells twice in 10 mL of sterile 1 M Sorbitol.

4. Resuspend cells in 10 mL SCE buffer.

5. Add 5–10 μL of 4 mg/mL Zymolyase 60,000 (Miles Laboratories). Incubate cells at 30° C. for about 30–60 minutes.

Since the preparation of spheroplasts is a critical step in the transformation procedure, one should monitor spheroplast formation as follows: add 100 μL aliquots of cells to 900 μL of 5% SDS and 900 μL of 1 M Sorbitol before or just after the addition of zymolyase and at various times during the incubation period. Stop the incubation at the point where cells lyse in SDS but not in sorbitol (usually between 30 and 60 minutes of incubation).

6. Wash spheroplasts twice in 10 mL of sterile 1 M Sorbitol by centrifugation at 1000 g for 5–10 minutes. (The time and speed for centrifugation may vary; centrifuge enough to pellet spheroplasts but not so much that they rupture from the force.)

7. Wash cells once in 10 mL of sterile CaS.

8. Resuspend cells in total of 0.6 mL of CaS. C. Transformation

1. Add DNA samples (up to 20 μL volume) to 12×75 mm sterile polypropylene tubes. (DNA should be in water or TE buffer; for maximum transformation frequencies with small amounts of DNA, it is advisable to add about 1 μL of 5 mg/mL sonicated *E. coli* DNA to each sample.)

2. Add 100 μL of spheroplasts to each DNA sample and incubate at room temperature for about 20 minutes.

3. Add 1 mL of PEG solution to each sample and incubate at room temperature for about 15 minutes.

4. Centrifuge samples at 1000 g for 5–10 minutes and decant PEG solution.

5. Resuspend samples in 150 μL of SOS and incubate for 30 minutes at room temperature.

6. Add 850 μL of sterile 1 M Sorbitol and plate aliquots of samples as described below. D. Regeneration of Spheroplasts 1. Recipe for Regeneration Agar Medium:
   a. Agar-Sorbitol- 9 g Bacto-agar, 54.6 g Sorbitol, 240 mL H₂O, autoclave.
   b. 10X Glucose- 20 g Dextrose, 100 mL H₂O, autoclave.
   c. 10X SC- 6.75 g Yeast Nitrogen Base without amino acids, 100 mL H₂O, autoclave. (Add any desired amino acid or nucleic acid up to a concentration of 200 μg/mL before or after autoclaving.)
   d. Add 30 mL of 10X Glucose and 30 mL of 10X SC to the melted Agar-Sorbitol solution to give a total of 300 mL. Add 0.6 mL of 0.2 mg/mL biotin and any other desired amino acid or nucleic acid to a concentration of 20 μg/mL. Hold melted Regeneration Agar at 55–60° C.

2. Plating of Transformation Samples:
   Pour bottom agar layer of 10 mL Regeneration Agar per plate at least 30 minutes before transformation samples are ready. Distribute 10 mL aliquots of Regeneration Agar to tubes in a 45–50° C. bath during the period that transformation samples are in SOS. Add aliquots of transformation samples described above to tubes with Regeneration Agar and pour onto bottom agar layer of plates. Add a quantity of each sample to 10 mL aliquots of melted Regeneration Agar held at 45–50° C. and pour each onto plates containing a solid 10 mL bottom agar layer of Regeneration Agar.

3. Determination of Quality of Spheroplast Preparation:
   Remove 10 μL of one sample and dilute 100 times by addition to 990 μL of 1 M Sorbitol. Remove 10 μL of the 100 fold dilution and dilute an additional 100 times by addition to a second 990 μL aliquot of 1 M Sorbitol. Spread plate 100 μL of both dilutions on YPD agar medium to determine the concentration of unspheroplasted whole cells remaining in the preparation. Add 100 μL of each dilution to 10 mL of Regeneration Agar supplemented with 40 μg/mL histidine to determine total regeneratable spheroplasts. Good values for a transformation experiment are $1-3 \times 10^7$ total regeneratable (spheroplasts/mL and about $1 \times 10^3$ whole cells/mL.

4. Incubate plates at 30° C. for 3–5 days.

EXAMPLE IV

Production of β-Galactosidase in *Pichia pastoris*

The production of β-galactosidase in transformed *Pichia pastoris* demonstrates the ability of yeast of the genus Pichia to be employed as a host/vector system for the production of polypeptide products. *Pichia pastoris* GS115 (NRRL Y-15851) was transformed with plasmid pSAOH5 (see FIG. 6) and grown up in minimal medium containing 0.5 μg/mL of biotin and 0.1% glucose at 30° C. until they reached stationary phase. The cells were then shifted to minimal medium containing 0.5 μg/mL of biotin and 0.5% methanol and grown for about 3–5 generations at 30° C. After this initial growth on methanol, cells were shifted to fresh minimal media containing 0.5 μg/mL biotin and 0.2% methanol as carbon source. The cells were incubated at 30° C. for about 80 hours, with samples periodically drawn to determine alcohol oxidase and β-galactosidase levels.

The first sample drawn, immediately after the cells were shifted to the growth medium, analyzed for over 500 units of alcohol oxidase and over 1100 units of β-galactosidase. Assay procedures employed are detailed in the appendix.

These results demonstrate the utility of *Pichia pastoris* as a host/vector system for the production of gene products in yeast. The plasmid employed to transform the host, plasmid pSAOH5, is a Pichia plasmid which codes for the production of β-galactosidase under the control of a methanol responsive regulatory region. The transformed strain used for this demonstration has been deposited with the Northern Regional Research Center and is available to the public under the accession number NRRL Y-15853.

The examples have been provided merely to illustrate the practice of our invention and should not be read so as to limit the scope of our invention or the appended claims in any way. Reasonable variation and modification, not departing from the essence and spirit of our invention, are contemplated to be within the scope of patent protection desired and sought.

APPENDIX

Alcohol Oxidase Assay

The alcohol oxidase activity for reaction with methanol was determined by the following assay procedure (dye-peroxidase method). A dye-buffer mixture was prepared by mixing 0.1 mL of an o-dianisidine solution (1 weight % o-dianisidine in water) with 12 mL of aerated 0.1 M sodium phosphate buffer (pH 7.5). The assay mixture was prepared with 2.5 mL of the dye-buffer mixture, 50 μL of methanol, 10 μL of a peroxidase solution (1 mg of horse-radish peroxidase-Sigma, Type II), and 25 μL of the alcohol oxidase solution. The assay mixture was maintained at 25° C. in a $4 \times 1 \times 1$ cm cuvette and the increase in absorbance by the dye at 460 nm was recorded for 2 to 4 minutes. The enzyme activity was calculated by $$\text{Activity (μ mole/min/mL or Enzyme Units/mL)} = \frac{\Delta A}{\text{min}} \times 11.5$$

wherein 11.5 is a factor based on a standard curve prepared with known aliquots of H₂O₂ and ΔA is the change in absorbance during the experimental interval.

β-Galactosidase Assay

β-Galactosidase was determined as follows: A. Solutions required:

| Z-buffer | | Final concentration |
| --- | --- | --- |
| Na₂HPO₄·7H₂O | 16.1 g | 0.06 M |
| NaH₂PO₄ | 5.5 g | 0.04 M |
| KCl | 0.75 g | 0.01 M |
| MgSO₄·7H₂O | 0.246 g | 0.001 M |
| 2-mercaptoethanol | 2.7 mL | 0.05 M | fill up to 1L; pH should be 7

O-Nitrophenyl-β-D-qalactoside (ONPG):
Dissolve 400 mg ONPG (Sigma N-1127) in 100 mL of distilled water to make a 4 mg/mL ONPG solution. B. Assay Procedure:

1. Withdraw an aliquot from the culture medium (0.1–0.5 OD₆₀₀ of yeast cells), centrifuge and wash cell pellet with water.
2. Add 1 mL of Z buffer to the cell pellet, 30 μL of CHCl₃ and 30 μL of 0.1% SDS, vortex, incubate 5 minutes at 30° C.

3. Start reaction by adding 0.2 mL of ONPG (4 mg/mL), vortex.
4. Stop reaction by adding 0.5 mL of a 1 M Na₂CO₃ solution at appropriate time points A₄₂₀<1).
5. Read absorbance of supernatant at 420 nm. C. Calculation of β-galactosidase Units:

1 U=1 nmole of orthonitrophenol (ONP) formed per minute at 30° C. and a pH 7.

1 nmole of ONP has an absorbance at 420 nm ($A_{420}$) of 0.0045 with a 1 cm pathlength; thus, an absorbance of 1 at 420 nm represents 222 nmole ONP/mL, or 378 nmole/1.7 mL since the total volume of supernatant being analyzed is 1.7 mL. Hence, Units are calculated as follows:

$$U = \frac{A_{420}}{t(\min)} \times 378$$

We claim:

1. A process for transforming a host yeast strain of *Pichia pastoris*, which is defective in at least one biosynthetic pathway, said process comprising:
   (a) contacting the host yeast strain with a sulfhydryl group reducing agent;
   (b) contacting the product cells of step (a) with a cell wall degrading reagent under conditions suitable for the formation and maintenance of spheroplasts;
   (c) contacting the spheroplasts generated in step (b) with a hybrid plasmid which is capable of functioning as a selectable marker to complement said defect under conditions suitable for transformation; and
   (d) treating the product of step (c) under cell wall regenerating conditions wherein said conditions suitable for the formation of spheroplasts comprise:
      (i) 10–100 μg of cell wall degrading reagent per 10 mL of cell suspension; wherein said cell suspension is prepared by suspending exponentially growing cells in SCE buffer;
      (ii) maintained at 25–35° C.;
      (iii) for 15–60 minutes;
   and wherein said contacting conditions suitable for transformation comprise:
      (i) 2–10 volumes of CaCl₂-polyethylene glycol solution per volume of spheroplast-containing suspension;
      (ii) maintained at 20–30° C.;
      (iii) for 5–30 minutes
   and where said cell wall regenerating conditions comprise:
      (i) adding transformed spheroplasts to regeneration agar, wherein said regeneration agar comprises:
         about 1 M sorbitol,
         about 0.1 M dextrose,
         about 7 g/L yeast nitrogen base, and
         about 3% agar;
      (ii) maintained at 25–35° C.;
      (iii) for about 3–10 days.

2. A process in accordance with claim 1 wherein said sulfhydryl group reducing agent is dithiothreitol.

3. A process in accordance with claim 1 wherein said cell wall degrading reagent is Zymolyase.

4. A process in accordance with claim 9 wherein said host yeast strain is defective in at least one amino acid biosynthetic pathway.

5. A process in accordance with claim 1 wherein said host yeast strain is defective in the histidine biosynthetic pathway.

6. A process in accordance with claim 5 wherein said histidine biosynthetic pathway is defective at the gene encoding histidinol dehydrogenase.

7. A process in accordance with claim 6 wherein said host yeast strain is *Pichia pastoris* NRRL Y-15851 (GS115).

8. A process in accordance with claim 1 wherein said hybrid plasmid comprises a functional gene which complements the defect in the biosynthetic pathway in which the host yeast strain is defective.

9. A process in accordance with claim 6 wherein said hybrid plasmid comprises a histidinol dehydrogenase encoding gene.

10. A process in accordance with claim 8 wherein said hybrid plasmid is plasmid pYA2.

11. A process in accordance with claim 8 wherein said hybrid plasmid is plasmid pYA4.

12. A process in accordance with claim 8 wherein said hybrid plasmid is plasmid pYJ30.

13. A process in accordance with claim 8 wherein said hybrid plasmid is plasmid pYJ32.

14. A process in accordance with claim 1 further comprising:
   (e) growing the product cells of step (d) under selective growth conditions.

15. A process in accordance with claim 9 further comprising:
   (e) growing the product cells of step (d) under selective growth conditions; wherein said selective growth conditions comprise growth on yeast minimal medium without added histidine.

16. A biologically pure *Pichia pastoris* NRRL Y-15851 (GS115).

17. A transformed host cell of *Pichia pastoris* wherein said host cell is defective in histidinol dehydrogenase transformed with a hybrid plasmid which comprises a functional gene which complements the defect in the histidinol dehydrogenase gene in which the host *Pichia pastoris* cell is defective.

18. A yeast cell in accordance with claim 17 wherein said functional gene is obtained from a yeast selected from the group consisting of Pichia and Saccharomyces.

* * * * *